US011957309B2

(12) United States Patent
Chu et al.

(10) Patent No.: US 11,957,309 B2
(45) Date of Patent: *Apr. 16, 2024

(54) MODULAR SCOPE DEVICE

(71) Applicant: BOSTON SCIENTIFIC SCIMED, INC., Maple Grove, MN (US)

(72) Inventors: Michael S. H. Chu, Brookline, MA (US); Sacha Tang, Lowell, MA (US); Mayur Kiran Patel, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,732

(22) Filed: Aug. 18, 2022

(65) Prior Publication Data
US 2022/0386852 A1 Dec. 8, 2022

Related U.S. Application Data

(63) Continuation of application No. 16/821,723, filed on Mar. 17, 2020, now Pat. No. 11,452,436.
(Continued)

(51) Int. Cl.
A61B 1/00 (2006.01)
A61B 1/005 (2006.01)
A61B 1/307 (2006.01)

(52) U.S. Cl.
CPC ...... *A61B 1/00135* (2013.01); *A61B 1/00094* (2013.01); *A61B 1/00098* (2013.01);
(Continued)

(58) Field of Classification Search
CPC ............ A61B 1/00098; A61B 1/00094; A61B 1/00105; A61B 1/00124; A61B 1/00128;
(Continued)

(56) References Cited

U.S. PATENT DOCUMENTS 5,419,311 A * 5/1995 Yabe ...................... A61B 1/015
600/124
6,165,123 A * 12/2000 Thompson ......... A61B 1/00078
600/152
(Continued)

FOREIGN PATENT DOCUMENTS

EP 2508120 A1 10/2012
EP 2692273 A1 2/2014
JP 2001286439 A 10/2001

OTHER PUBLICATIONS

Office Action in Chinese Application No. 202080016322.9, dated Nov. 21, 2023 (9 pages).

*Primary Examiner* — Aaron B Fairchild
(74) *Attorney, Agent, or Firm* — Bookoff McAndrews, PLLC

(57) ABSTRACT

A system for modularly assembling a scope device includes an optical module which has an optical housing and a longitudinal member extending distally therefrom. A distal end of the member includes a camera for visualizing a target area, electric wires and a light source extending from the camera to the optical housing. The system also includes a deflector module coupleable with the optical module. The deflector module includes a deflector housing and a deflector shaft extending distally therefrom. The shaft includes a first channel sized, shaped and configured to receive the member therein and a deflectable portion extending along a distal portion of the shaft. The deflector housing includes an actuator for deflecting the deflectable portion, the optical and deflector housings including corresponding connecting elements to engage one another when the member is inserted through the first channel and the deflector and optical housings are coupled.

12 Claims, 2 Drawing Sheets

Related U.S. Application Data

(60) Provisional application No. 62/837,349, filed on Apr. 23, 2019.

(52) U.S. Cl.
CPC ...... *A61B 1/00124* (2013.01); *A61B 1/00128* (2013.01); *A61B 1/00195* (2013.01); *A61B 1/005* (2013.01); *A61B 1/0057* (2013.01); *A61B 1/307* (2013.01)

(58) Field of Classification Search
CPC ............ A61B 1/00135; A61B 1/00195; A61B 1/0057; A61B 1/00142; A61B 1/018; A61B 1/0125
See application file for complete search history.

(56) References Cited

U.S. PATENT DOCUMENTS

| | | |
|---|---|---|
| 8,333,691 B2 | 12/2012 | Schaaf |
| 9,339,173 B2 | 5/2016 | McWeeney et al. |
| 2002/0022763 A1* | 2/2002 | Sano ...................... H04N 23/56 |
| | | 348/E5.029 |
| 2005/0090709 A1 | 4/2005 | Okada et al. |
| 2005/0272975 A1* | 12/2005 | McWeeney ....... A61M 25/0068 |
| | | 600/172 |
| 2006/0252993 A1 | 11/2006 | Freed et al. |
| 2011/0263933 A1 | 10/2011 | Schaaf |
| 2015/0057537 A1* | 2/2015 | Dillon .................. A61B 1/0014 |
| | | 600/113 |
| 2017/0332882 A1 | 11/2017 | Yamamoto et al. |
| 2019/0053861 A1 | 2/2019 | Lwin et al. |

\* cited by examiner

MODULAR SCOPE DEVICE

PRIORITY CLAIM

The present application is a Continuation of U.S. patent application Ser. No. 16/821,723 filed on Mar. 17, 2020, which claims priority to U.S. Provisional Patent Application Ser. No. 62/837,349 filed Apr. 23, 2019. The disclosures of the above application(s)/patent(s) are incorporated herewith by reference.

BACKGROUND

Flexible ureteroscopes are often used in the examination of kidneys and may include treatments such as, for example, intracorporeal lithotripsy, treatment of upper urinary tract urothelial malignancies, incising strictures, evaluation of ureteral trauma, and repairing ureteropelvic junction obstructions. In particular, for the treatment of kidney and ureteral stones, ureteroscopes may be used in conjunction with other medical devices such as, for example, guidewires, retrieval devices and laser fibers to fragment and/or pulverize kidney stones and remove the debris from the body. In one example, kidney stones are fragmented into portions which are removed from the body via, for example, basket retrieval. In another example, kidney stones are dusted—e.g., pulverized into extremely fine fragments—so that the fragments may be passed spontaneously and/or removed from the body via suction. Stone dust in the lower poles, however, will most likely not drain or pass spontaneously. Thus, urologists will relocate the lower pole stones to the upper poles prior to dusting.

Single-use flexible ureteroscopes such as, for example, the LithoVue™ flexible ureteroscope, are disposed of after a single procedure, even if they are in good working order. Single-use ureteroscopes may be used to prevent infection, which can occur from patient to patient, from environment to patient or from organisms within the patient body. Flexible ureteroscope devices are prone to mechanical (e.g., pull wire or fiber-optic) damage, particularly when attempting difficult access such as overloaded deflection when reaching the lower pole of the kidney to remove kidney stones. Single-use ureteroscopes may be well worth the cost for more difficult procedures—e.g., procedures requiring lower pole access—when compared to the repair cost of a reusable scope. In some cases, however—e.g., procedures requiring simple upper pole access—disposing of a single-use ureteroscope that is still in good working condition may be considered costly.

SUMMARY

The present disclosure relates to a system for modularly assembling a scope device, comprising an optical module including an optical housing and a longitudinal member extending distally therefrom, a distal end of the longitudinal member including a camera for visualizing a target area within a body accessible via a body lumen, electric wires and a light source extending from the camera, through the longitudinal member and to the optical housing, and a deflector module coupleable with the optical module, the deflector module including a deflector housing and deflector shaft extending distally therefrom, the deflector shaft including a longitudinally extending first channel sized, shaped and configured to receive the longitudinal member therein and a deflectable portion extending along a distal portion of the deflector shaft, the deflector housing including an actuator for deflecting the deflectable portion, the optical housing and the deflector housing including corresponding connecting elements configured to engage one another when the longitudinal member is inserted through the first channel and the deflector housing and the optical housing are coupled.

In an embodiment, the deflector shaft may further include a second channel extending therethrough.

In an embodiment, the first channel may be one of (i) a dedicated optical channel sized, shaped and configured to correspond to the longitudinal member of the optical module and (ii) a working channel configured to receive both the longitudinal member of the optical module and one of a medical device and a suction force therethrough.

In an embodiment, when the first channel is the dedicated optical channel, a distal end of the first channel may be sealed via a lens.

In an embodiment, the deflectable portion may be deflected via pull wires extending from the deflectable portion to the deflector housing such that the actuator is movable relative to the deflector housing to move the deflectable portion bidirectionally within a permitted range of deflection.

In an embodiment, the deflectable portion may include a port attached to the deflectable housing and in communication with a proximal end of the first channel such that the longitudinal member is insertable into the first channel via the port.

In an embodiment, the port may include a valve which seals about a proximal portion of the longitudinal member.

In an embodiment, the system may further comprise a channel module coupleable with the deflector module, the channel module including a channel shaft extending longitudinally from a proximal end to a distal end, the channel module including a lumen extending longitudinally therethrough from the proximal end to the distal to receive the deflector shaft and a working channel extending along a length of the channel shaft to the distal end, a hub extending laterally from the channel shaft so that a channel extending through the hub is in communication with the working channel.

In an embodiment, the channel module may include a lens sealed over a distal end of the lumen.

In an embodiment, the system may further comprise a sheath module including a sheath extending from a proximal end to a distal end and including a sheath channel sized, shaped configured to receive the longitudinal member of the optical module therein, a distal opening of the sheath channel being sealed via a lens and the proximal end of the sheath including a connector configured to engage a proximal portion of the longitudinal member.

In an embodiment, the lens may be one of polarized, concave, convex, meniscus, a neutral optical lens, laser resistant, and fish eye.

In an embodiment, one of the deflector housing and the optical housing may be sealed to be water resistant such that contaminants are washably removed from the one of the deflector housing and the optical housing.

The present disclosure also relates to a system for modularly assembling a scope device, comprising an optical module including an optical housing and a longitudinal member extending distally therefrom, a distal end of the longitudinal member including a camera for visualizing a target area within a body accessible via a body lumen, electric wires and a light source extending from the camera, through the longitudinal member and to the optical housing, and a channel module coupleable with the optical module, the channel module including a channel shaft extending longitudinally from a proximal end to a distal end, the channel module including a lumen extending longitudinally therethrough from the proximal end to the distal to receive the longitudinal member and a working channel extending along a length of the channel shaft to the distal end, a hub extending laterally from the channel shaft so that a channel extending through the hub is in communication with the working channel.

In an embodiment, the channel module may include a lens sealed over a distal end of the lumen.

In an embodiment, the lens may be one of polarized, concave, convex, meniscus, a neutral optical lens, laser resistant, and fish eye.

The present disclosure also relates to a method for accessing a target area within a body via a body lumen, comprising assembling an optical module with a deflector module by inserting a longitudinal member of the optical module through a first channel of a deflector shaft of the deflector module and coupling an optical housing at a proximal end of the longitudinal member with the deflector housing at a proximal end of the deflector shaft, inserting the assembled longitudinal member and the deflector shaft to a target area via a body lumen, imaging the target area via a camera at a distal of the longitudinal member, and deflecting a distal portion of the deflector shaft to image a target stone in the target area.

BRIEF DESCRIPTION

DETAILED DESCRIPTION

Figure 1:
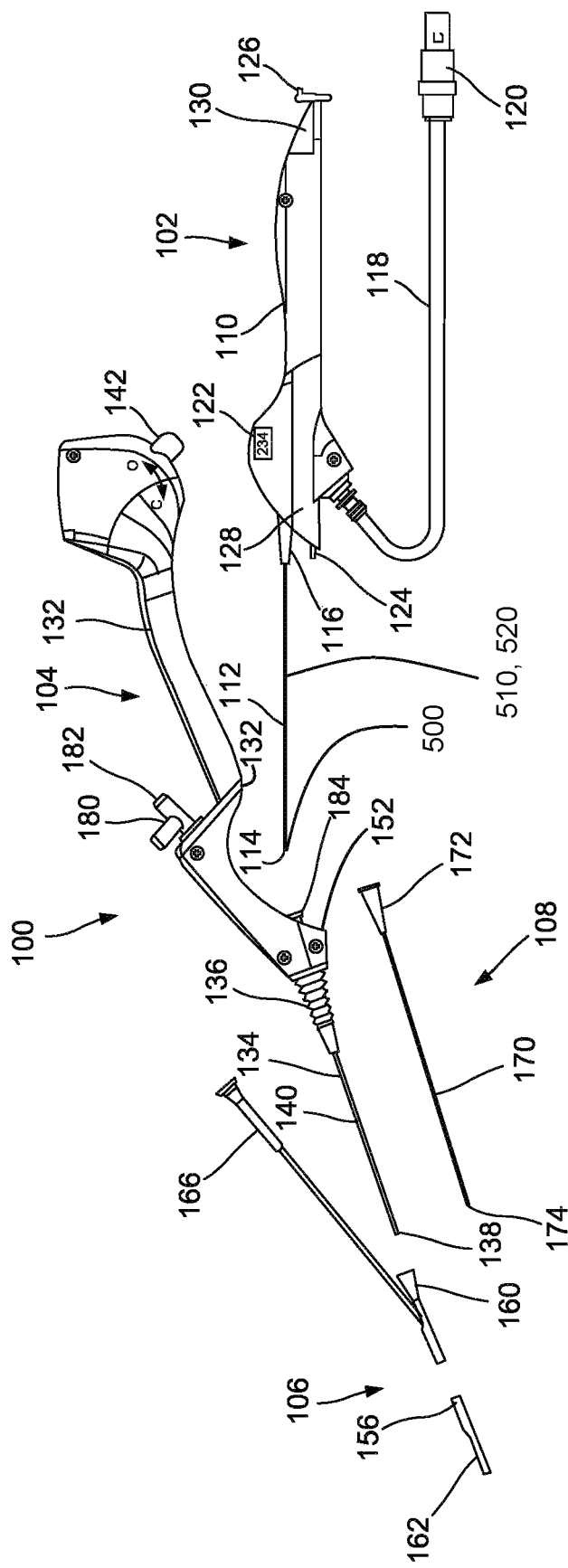
FIG. 1 shows an exploded side view of a system according to the exemplary embodiment of the present disclosure.

The present disclosure may be further understood with reference to the following description and appended drawings, wherein like elements are referred to with the same reference numerals. The present disclosure relates to disposable scope systems for accessing, examining or treating a body lumen or a body cavity and, in particular, relates to modular scope systems which allow for modular assembly of a scope device so that the scope device is configured to suit a particular procedure. The modular system also allows portions of the scope device to be replaces when damaged or when the scope device is to be reused.

The exemplary embodiments describe a modular flexible scope system comprising an optical module for facilitating visualization of a target area and/or a target stone to be treated, a deflector module facilitating a deflection of a deflectable distal portion for accessing the target area and/or stone, a channel module via which medical devices (e.g., guidewires retrieval device, laser fibers) may be inserted into the target area, and a sheath module configured to provide a protective barrier for portions of the optical module. The optical module, deflector module, channel module and the sheath module may be assembled and/or replaced, as necessary, as will be described in further detail below. Although the exemplary embodiments specifically describe a ureteroscope for treating ureteral or kidney stones, it will be understood by those of skill in the art that the system of the present disclosure may be adapted for other purposes such as, for example, tissue biopsy retrieval. It should be noted that the terms "proximal" and "distal", as used herein, are intended to refer to a direction toward (proximal) and away from (distal) a user of the device (e.g., physician).

As shown in FIG. 1, a modular scope system 100 according to an exemplary embodiment of the present disclosure comprises an optical module 102 for visualizing a target stone to be treated and/or a target area within a body in which, for example, the target stone is located, a deflector module 104 for facilitating deflection of a distal deflectable portion to visualize and/or access the target area or stone, a channel module 106 for providing a working channel via which a medical device (e.g., guidewire, laser fiber, retrieval device) may be inserted to the target area, and a sheath module 108 for providing a protective barrier over portions of the optical module and, in some cases, for providing a working channel. As will be described in further detail below, the optical module 102 is assembled with at least one of the deflector module 104, the channel module 106 and the sheath module 108, as desired, to treat a target stone. The assembly of modules may be changed during the procedure, if necessary, to reconfigure or repair the assembly.

The optical module 102 comprises a housing 110 and a tubular member 112 extending distally therefrom to a distal end 114 including a camera 500. The housing 110 is sealed such that the housing 110 is water tight and/or water resistant so that the optical module 102 may be cleansed of contamination. In one embodiment, a strain relief 116 extends distally from the housing 110 so that the tubular member 112 extends distally therefrom. Electronics (e.g., pressure sensors, temperature sensors, GPS, batteries, antenna, receivers, switches, buttons, controllers) and a light source for facilitating visualization of the target stone and/or the target area via the camera 500 are housed within the housing 110. In this embodiment, electric wires 510 and a light fiber 520 extend from the housing 110, through the strain relief 116 and the tubular member 112 to the camera 500 at the distal end 114.

In this embodiment, the optical module 102 further comprises a cable 118 extending from the housing 110 to include a plug 120 which may be plugged into a console for providing power to the optical module 102 and for displaying an image detected via the camera to a user (e.g., urologist). In another embodiment, however, the optical module 102 includes rechargeable batteries and elements configured to provide a wireless connection (e.g., Bluetooth) with the console so that the cable 118 and plug 120 are not required. In a particular embodiment, the optical module 102 includes a digital clock 122 showing a remaining life of the optical module 102. The digital clock 122 may, for example, be located on the housing 110.

The optical module 102 further includes connecting elements such as for example, a tongue 124 and a hook 126, which are configured to engage corresponding connecting elements of the deflector module 104 to couple the housing 110 of the optical module 112 to a portion of the deflector module 104, as will be described in further detail below. In one example, the tongue 124 extends distally from a distal end 128 of the housing 110 while the hook 126 extends proximally from a proximal end 130 of the housing 110.

The deflector module 104 comprises a housing 132 and a shaft 134 extending distally therefrom. The shaft 134 in this embodiment is supported by a strain relief 136 extending distally from the housing 132. The shaft 134 is configured so that a distal portion 138 thereof is deflectable. Thus, the distal portion 138 is flexible while a proximal portion 140 may be reinforced with a coil or braid. In one example, the deflector module 104 includes two pull wires 144 extending from the housing 132, through the shaft 134 such that distal ends of the pull wires 144 are connected to the deflectable distal portion 138.

The pull wires 144 may be positioned, for example, opposite one another with proximal ends of the pull wires 144 connected to, for example, a control knob 142 attached to the housing 132 to control deflection of the deflectable distal portion 138. In one example, the control knob 142 may be rotated to deflect the deflectable distal portion 138 as desired. The control knob 142 may be rotated in two directions for bidirectional deflection of the distal portion 138. It will be understood by those of skill in the art, however, that the deflector module 104 may include ay of a variety of actuators and/or mechanisms for actuating a deflection of the distal portion 138.

Figure 3:
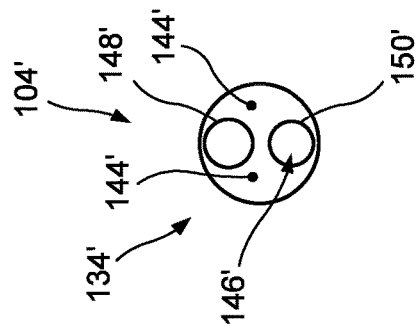
FIG. 3 shows a plan view of a distal end of a shaft of a deflector module according to an alternate embodiment.
Figure 2:
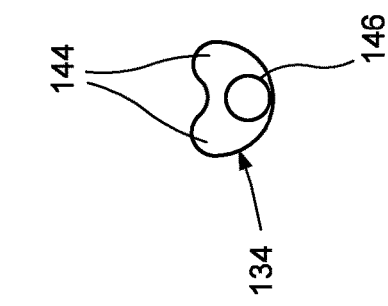
FIG. 2 shows a plan view of a distal end of a shaft of a deflector module of the system of FIG. 1.

The shaft 134 includes a channel 146 extending longitudinally therethrough. The channel 146 is configured to receive the tubular member 112 of the optical module 102 therein. In one embodiment, as shown in FIG. 2, the channel 146 is a dedicated optical channel that is specifically sized and shaped to receive only the tubular member 112. In another embodiment, the channel 146 is sized and shaped so that the tubular member 112 may share the channel 146 with a medical device to be inserted therethrough. In yet another embodiment, as shown in FIG. 3, a deflector module 104' including a shaft 134' is substantially similar to the deflector module 104. The shaft 134', however, includes a working channel 148' in addition to a channel 146'. As would be understood by those skilled in the art, the working channel 148' may be configured such that a medical device may be inserted to the target stone and/or target area therethrough. Similarly to the shaft 134, pull wires 144' for deflecting a distal portion thereof extend therealong.

In one embodiment in which the channel 146' is a dedicated optical channel and the shaft 134' includes the separate working channel 148', a distal opening of the channel 146' may further include a lens 150' to protect the camera at the distal end 114 of the tubular member 112 received therein. The lens 150' seals the distal opening of the channel 146 and may be polarized, concave, meniscus, a neutral optical lens, laser resistant, fish eye, etc. as would be understood by those skilled in the art. The lens 150' may include indicator markings to enable the user to compare and/or measure the size of target objects such as, for example, stones. In one embodiment, the lens 150' may be configured as a cap to seal the distal opening of the channel 146'. The lens 150' provides a protective barrier for the tubular member 112 of the optical module 102 such that upon completion of a procedure, the deflector module 104 may be disposed of while the optical module 102 may be cleaned and reused. In another embodiment, the channel 146' may be sized to accommodate both the tubular member 112 and another medical device and/or a suction force therein. In this embodiment, the channel 146' does not include a lens.

Depending on a number of channels extending through the shaft 134, 134', the deflector module 104, 104' includes a connector 180 including at least one hub 182, each of the at least one hub 182 configured to communicate with a corresponding one of the channels. For example, where a medical device is configured to be insertable through both a channel 146' and an additional working channel 148' of the deflector module 104, the connector 180 will include two hubs 182, each of the hubs 182 in communication with a corresponding one of the channels 146, 148' so that a medical device may be inserted through each of the channels 146', 148' via one of the hubs 182.

In one embodiment, the housing 132 of the deflector module 104 includes corresponding connecting elements configured to engage, for example, the tongue 124 and the hook 126 of the housing of the optical module 102. Corresponding connecting elements may include, for example, a slot 152 along a distal portion of the housing 132 sized and shaped to receive the tongue 124 and a ledge 154 along proximal portion of the housing 132 configured to receive or otherwise engage portion of the hook 126 to lock the housing 110 of the optical module 102 with the housing 132 of the deflector module 110.

It will be understood by those of skill in the art, however, that the housings 110, 132 may include any of a variety of corresponding connecting elements configured to couple and/or lock the housings 110, 132 relative to one another. It will also be understood by those of skill in the art that the housings 110, 132 may be correspondingly shaped so that, when coupled to one another, the assembled housings 110, 132 form a handle member that may be easily handled via the user during a desired procedure. When coupling the housing 110 with the housing 132, the tubular member 112 must first be inserted into the shaft 134 via, for example, a port 184 connected to the housing 132 and in communication with the channel 146 of the shaft 134. The port 184 may include a valve (e.g., duckbill valve), which seals about, for example the strain relief 116.

Figure 4:
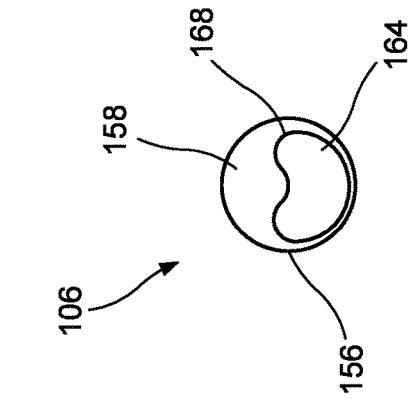
FIG. 4 shows a plan view of a distal end of a shaft of a channel module of the system of FIG. 1.

In one embodiment, as shown in FIG. 4, the channel module 106 is configured to be assembled with the shaft 134 of the deflector module 104 to provide an additional working channel 158 via which a medical device may be inserted to the target area, if necessary. In particular, the channel module 116 comprises a shaft 156 extending longitudinally from a proximal end 160 configured to be connected to, for example, the strain relief 136 of the deflector module 104, to a distal end 162. The shaft 156 includes a lumen 164 extending longitudinally therethrough from the proximal end 160 to the distal end 162, the lumen 164 being sized, shaped and otherwise configured to receive the shaft 134 of the deflector module 104 therein. The working channel 158 also extends along a length of the shaft 156. The channel module 106 also includes a connector such as, for example, a hub 166 extending laterally from the shaft 156. A channel of the hub 166 is in communication with the working channel 158 so that a medical device may be inserted through the hub 166 to gain access to the working channel 158. Although the exemplary embodiment only shows and describes one working channel 158, it will be understood by those of skill in the art that the shaft 156 of eh channel module 106 may include more than one working channel, each of which will include a separate hub.

In one embodiment, the channel module 106 may be assembled with the deflector module 104, as shown in FIG. 2, in which the channel 146 is a dedicated optical channel and does not include a separate working channel. In this embodiment, the channel module 106 includes a lens 168 sealing a distal opening of the lumen 164, which is configured to receive the shaft 134 of the deflector module 104. The lens 168 may be substantially similar to the lens 150' as described above with respect to the deflector module 104' shown in FIG. 3. In this embodiment, the lens 168 seals the lumen 164 providing a protective barrier over the shaft 134 so that upon completion of a procedure, the channel module 106 may be disposed of while the deflector module 104 and/or the optical module 102 may be cleaned and reused.

Figure 5:
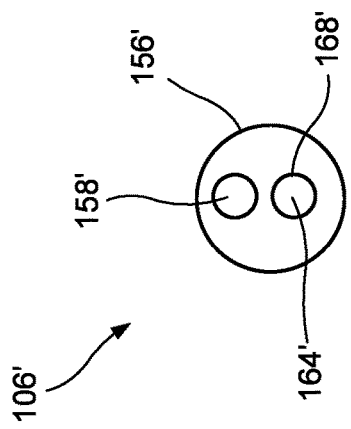
FIG. 5 shows a plan view of distal end of a channel module according to an alternate embodiment.

According to another embodiment, as shown in FIG. 5, a channel module 106' is substantially similar to the channel module 106. A lumen 164' of the shaft 156', however, may be sized, shaped and configured to receive the tubular member 112 of the optical module 102. The channel module 106' may be particularly suited for cases in which a distal portion is not required to be deflected to properly visualize the target stone and/or target area—e.g., a simple procedure in the upper pole. A distal opening of the lumen 164' may be similarly sealed with a lens 168' for protecting the tubular member 112 and the camera at the distal end 114 thereof. In this embodiment, a working channel 158' extending through the shaft 156' is substantially similar to the working channel 158.

Figure 6:
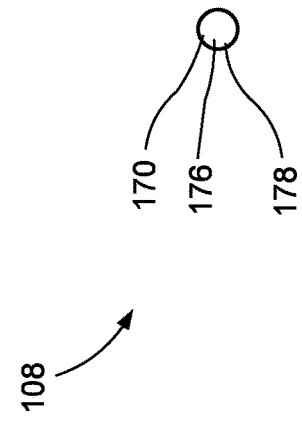
FIG. 6 shows a plan view of a distal end of a sheath module of the system of FIG. 1.

In one embodiment, the sheath module 108 is configured to be coupled to the optical module 102 prior to assembly of the optical module 102 with the deflector module 104. The sheath module 108 includes a sheath 170 extending from a proximal end 172 including a connector configured to be coupled to, for example, the strain relief 116 of the optical module 102 to a distal end 174. As shown in FIG. 6, the sheath 170 includes a channel 176 extending therethrough and a lens 178 sealing a distal opening thereof. The lens 178 may be substantially similar to the lens 150' described above with respect to the deflector module 104.

As discussed above, the optical module 102 of the system 100 may be assembled with at least one of the deflector module 104, the channel module 106 and the sheath module 108. According to one exemplary method for assembly in which laser lithotripsy with removal is to be utilized, the optical module 102 may first be assembled with the sheath module 108. In particular, the tubular member 112 of the optical module 102 is inserted through the channel 174 of the sheath 170 until the proximal end 172 of the sheath 170 engages the strain relief 116 of the optical module 102. In this embodiment, the tubular member 112, with the sheath 170 assembled thereover, is then inserted through the port 184 and into the channel 146' of the shaft 134' of the deflector module 104' shown in FIG. 3.

In this embodiment, the channel 146' is configured to accommodate both the tubular member 112 and a suction force therein. Once the optical module 102, the deflector module 104' and the sheath module 130 have been assembled, the shaft 134' may be inserted through a body lumen to the target stone. A laser fiber may be inserted through the working channel 148' to the target area to apply laser energy to the stone to duct the stone into fine fragments. The stone fragments may then be suctioned from the target area via a suction force applied through the channel 146', about the tubular member 112. As described above, each of the channels 146', 148' may be separately accessed via one of the hubs 182. In this embodiment, since the sheath module 108 provides a protective barrier for the optical module 102, the deflector module 104' and the sheath module 108 may be disposed of while the optical module is cleaned for reuse.

According to another embodiment, in which the channel 146' of the shaft 134' of the deflector module is a dedicated optical channel, the optical module 102 is not required to be assembled with the sheath module 108' prior to assembly with the deflector module 104. In this embodiment, the optical module 102 is coupled directly to the deflector module 104'. As described above, a laser fiber is inserted into the working channel 148' to dust the target stone. Upon dusting of the target stone, however, the laser fiber may be removed so that a suction force may be applied through the working channel 148' to remove the dusted stone fragments from the body. In this embodiment, the lens 150' seals the distal opening of the channel 146' so that upon completion of the procedure, the deflector module 104' may be disposed of while the optical module 102 is cleaned and reused. The optical module 102 may then be assembled with a new deflector module 104 or 104' for subsequent use.

Alternatively, the optical module 102 may be assembled with the deflector module 104 and the channel module 106. In this embodiment, the channel 146 of the shaft 134 of the deflector module 104 may be a dedicated optical channel. Upon assembly of the optical module 102 with the deflector module 104 via insertion of the tubular member 112 into the channel 146 of the shaft 134, the assembled shaft 134 and tubular member 112 may be assembled with the channel module to provide the working channel 158. In this embodiment, once the optical module 102 and the deflector module 104 have been coupled as described above, the shaft 134 may be inserted through the lumen 164 of the shaft 156 of the channel module 106 until the proximal end 160 of the shaft 156 engages the strain relief 136 of the deflector module 104. The assembly may then be inserted through the body lumen to the target stone.

A laser fiber may be inserted through the working channel 158 to dust or fragment the target stone. Upon fragmentation, the laser fiber may be removed from the working channel 158 so that suction force may be applied therethrough to suction of the fine fragments of stone from the body. Alternatively, a retrieval device may be inserted through the working channel 158 to retrieve larger fragments of stone. Since the shaft 134 of the deflector module 104 and the tubular member 112 of the optical module 102 are protected via the lens 168 at the distal end of the lumen 164 of the channel module 106, upon completion of the procedure, the channel module 106 may be disposed of while the optical module 102 and the deflector module 104 may be cleaned of contamination and reused.

Although the exemplary embodiments describe specific assemblies of the optical module 102, the deflector module 104, the channel module 106 and the sheath module 108, it will be understood by those of skill in the art that the modules 102-108 of the system 100 may be assembled in any of a variety of configurations to suit a user's particular needs. It will also be understood by those of skill in the art that if at any point any of the assembled modules 102-108 is damaged in any way, the damaged module may be replaced without replacing those modules that are in good working condition.

Although the optical module 102 and the deflector module 104 are shown and described as two separate modules, in another embodiment, the optical module 102 and the deflector module 104 may be formed as a single module including a shaft with a deflectable distal portion and optical capabilities, which may be configured as, for example, a camera at a distal end of the deflectable portion. The combined optical and deflector module may be assembled with, for example, the channel module 106 via insertion through the lumen 164 such that the assembled device is provided with the working channel 158.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A system for modularly assembling a scope device, comprising:
   an optical module including an optical housing and a longitudinal member extending distally therefrom, a distal end of the longitudinal member including a camera for visualizing a target area within a body accessible via a body lumen, electric wires and a light fiber extending from the camera, through the longitudinal member and to the optical housing;
   a channel module couplable with the optical module, the channel module including a channel shaft extending longitudinally from a proximal end to a distal end and a working channel extending along a length of the channel shaft to the distal end, the channel module including a lumen extending longitudinally therethrough from the proximal end to the distal end to receive the longitudinal member, the channel module further including a hub extending laterally from the channel shaft so that a channel extending through the hub is in communication with the working channel; and
   a deflector module couplable with the channel module, the deflector module including a deflector shaft extending distally, the deflector shaft including a longitudinally extending first channel sized, shaped and configured to receive the longitudinal member of the optical module, the deflector shaft being sized, shaped and configured to be received by the lumen of the channel module.

2. The system of claim 1, wherein the channel module includes a lens sealed over a distal end of the lumen.

3. The system of claim 2, wherein the lens is one of polarized, concave, convex, meniscus, a neutral optical lens, laser resistant, and fish eye.

4. The system of claim 1, further comprising a sheath module including a sheath extending from a proximal end to a distal end and including a sheath channel sized, shaped and configured to receive the longitudinal member of the optical module therein, a distal opening of the sheath channel being sealed via a lens and the proximal end of the sheath being configured to couple to a proximal portion of the longitudinal member.

5. The system of claim 1, wherein the channel module further comprises a further working channel.

6. The system of claim 1, wherein the deflector shaft further includes a second channel extending therethrough.

7. The system of claim 1, wherein the first channel is one of (i) a dedicated optical channel sized, shaped and configured to correspond to the longitudinal member of the optical module or (ii) a working channel configured to receive both the longitudinal member of the optical module and one of a medical device and a suction force therethrough.

8. The system of claim 1, wherein the deflector module further comprises:
   a deflector housing including an actuator for deflecting a deflectable portion extending along a distal portion of the deflector shaft, the optical housing and the deflector housing including corresponding connecting elements configured to engage one another when the longitudinal member is inserted through the first channel and the deflector housing and the optical housing are coupled.

9. The system of claim 8, wherein the deflectable portion is configured to be deflected via pull wires extending from the deflectable portion to the deflector housing such that the actuator is movable relative to the deflector housing to move the deflectable portion bidirectionally within a permitted range of deflection.

10. The system of claim 8, wherein the deflectable portion includes a port attached to the deflectable housing and in communication with a proximal end of the first channel such that the longitudinal member is insertable into the first channel via the port.

11. The system of claim 10, wherein the port includes a valve configured to seal about a proximal portion of the longitudinal member.

12. The system of claim 8, wherein one of the deflector housing or the optical housing is sealed to be water resistant.

* * * * *